(12) United States Patent
Bischoff et al.

(10) Patent No.: US 8,298,564 B2
(45) Date of Patent: Oct. 30, 2012

(54) TWO PART ANTIMICROBIAL BOOT

(75) Inventors: Thomas C Bischoff, Minneapolis, MN (US); Jennifer E Raeder-Devens, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 1554 days.

(21) Appl. No.: 11/535,793

(22) Filed: Sep. 27, 2006

(65) Prior Publication Data

US 2008/0125728 A1    May 29, 2008

(51) Int. Cl.
*A61F 2/00* (2006.01)
*A01N 37/18* (2006.01)

(52) U.S. Cl. ........................... 424/423; 514/154
(58) Field of Classification Search .............. None
See application file for complete search history.

(56) References Cited

U.S. PATENT DOCUMENTS

| | | | |
|---|---|---|---|
| 5,217,493 A | 6/1993 | Raad | |
| H1465 H | 7/1995 | Stokes | |
| 5,624,704 A | 4/1997 | Darouiche et al. | |
| 5,820,607 A | 10/1998 | Tcholakian et al. | |
| 5,902,283 A | 5/1999 | Darouiche | |
| 5,997,815 A | 12/1999 | Anders et al. | |
| 6,099,562 A | 8/2000 | Ding et al. | |
| 6,162,487 A | 12/2000 | Darouiche | |
| 6,599,275 B1 | 7/2003 | Fischer, Jr. | |
| 6,887,270 B2 | 5/2005 | Miller | |
| 6,908,624 B2 | 6/2005 | Hossainy et al. | |
| 6,968,234 B2 | 11/2005 | Stokes | |
| 6,996,952 B2 | 2/2006 | Gupta et al. | |
| 7,596,408 B2 | 9/2009 | Singhal | |
| 2003/0224033 A1 | 12/2003 | Li et al. | |
| 2003/0224054 A1 | 12/2003 | Gibbins et al. | |
| 2004/0043052 A1 | 3/2004 | Hunter et al. | |
| 2004/0186528 A1 | 9/2004 | Ries | |
| 2005/0008528 A1* | 1/2005 | Prabhu et al. ............ 422/1 |
| 2005/0048121 A1 | 3/2005 | East et al. | |
| 2005/0079199 A1 | 4/2005 | Heruth | |
| 2005/0226931 A1 | 10/2005 | Gibbins et al. | |
| 2005/0249697 A1 | 11/2005 | Uhrich et al. | |
| 2005/0267543 A1 | 12/2005 | Heruth | |
| 2006/0009806 A1 | 1/2006 | Heruth | |
| 2006/0039946 A1 | 2/2006 | Heruth | |
| 2006/0051392 A1 | 3/2006 | Heruth | |
| 2006/0051393 A1 | 3/2006 | Heruth et al. | |
| 2006/0089705 A1 | 4/2006 | Ding et al. | |
| 2006/0116752 A1 | 6/2006 | Norton et al. | |
| 2006/0127438 A1 | 6/2006 | Hunter et al. | |
| 2006/0188546 A1 | 8/2006 | Giroux | |

FOREIGN PATENT DOCUMENTS

| | | |
|---|---|---|
| EP | 640661 | 3/1995 |
| WO | WO 96/39215 | 12/1996 |
| WO | WO 97/46268 | 12/1997 |
| WO | WO 2004/084955 | 10/2004 |
| WO | WO 2005/058414 | * 6/2005 |

OTHER PUBLICATIONS

Schierholz, et al., Journal of Antimicrobial Chemotherapy (2000) 46, 46-50.
Darouiche, et al., Antimicrobial Agents and Chemotherapy (Feb. 2002), p. 543-545.
Kohnen, et al., "Develment of a long-lasting ventricular catheter impregnated with a combination of antibiotics," Biomaterials (2003) 24, 4865-4869.
Shierholz, "Physico-chemical properties of a rifampin-releasing polydimethyl-siloxane shunt," Biomaterials (1997) 18, 634-641.
Reitz, "Clean beyond the white glove test," Medical Design Magazine, Sep. 13, 2001.
"Sterilization for Beginners," Medical Design Magazine, Jun. 18, 2004.
Elston, "Sterilization—Helping packaging stand up to sterilization,"Pharmaceutical & Medical Packaging News, Dec. 2005.
PCT International Search Report dated Apr. 7, 2008.

* cited by examiner

*Primary Examiner* — Scott Long
*Assistant Examiner* — Lyndsey Beckhardt (57) ABSTRACT

A system comprising an implantable medical device and a second polymeric layer configured to be disposed on or about the implantable medical device is described. The device includes a first polymeric layer into which a first therapeutic agent is incorporated. A second therapeutic agent is incorporated into the second polymeric layer. The device is sterilized by a first sterilization method. The second polymeric layer is sterilized by a second sterilization method. A method for making a sterile implantable medical system is also described. The method includes incorporating a first therapeutic agent in a first polymeric material and disposing the first polymeric material on or about an implantable medical device. The first polymeric material and the implantable medical device are sterilized by a first sterilization method. The method further includes incorporating a second therapeutic material in a second polymeric material and disposing the second polymeric material on or about the sterilized first polymeric material and implantable medical device. The second polymeric material is sterilized by a second sterilization method.

14 Claims, 9 Drawing Sheets

TWO PART ANTIMICROBIAL BOOT

FIELD

This application relates to medical devices and methods of sterilizing medical devices; particularly drug-containing devices and more particularly minocycline and rifampin-containing devices.

BACKGROUND

Implantable medical devices increasingly incorporate drugs to improve the performance of the medical device or reduce side effects associated with implantation of the device. Sterilization processes suitable for medical devices that do not incorporate drugs may not be suitable for such devices that incorporate drugs, due to incompatibilities of the sterilization process and the drugs. Examples of sterilization processes include steam sterilization (e.g., autoclaving), chemical sterilization (e.g., ethylene oxide or vaporized hydrogen peroxide), and sterilization via radiation (e.g., gamma or e-beam). Steam sterilization may not be compatible with drugs that degrade under high temperature or humidity conditions. Chemical sterilization may not be compatible with drugs that have chemical groups that react with the sterilization chemical, such as ethylene oxide. Radiation typically alters the chemical structures of drugs incorporated into medical devices. Accordingly, some drugs may be incompatible with radiation sterilization and may be more or less sensitive to gamma versus e-beam radiation, depending on the nature of the specific drug.

With regard to radiation sterilization, gamma radiation is capable of penetrating much further into a product or packaging than e-beam radiation because gamma radiation is higher energy radiation than e-beam. As such, gamma radiation may be preferred to e-beam in certain situations where the product is thick or dense and sterility throughout must be demonstrated. However, due to the set up of typical sterilization facilities, products sterilized by gamma radiation may be over sterilized or exposed to gamma radiation for a longer time than is needed to achieve sufficient sterilization. On the other hand, facilities for e-beam sterilization are typically more capable of limiting exposure of a product to the amount of radiation energy necessary to achieve sufficient sterilization. Accordingly, e-beam sterilization can be gentler than gamma radiation to products and their packaging. Regardless of the sterilization process employed, the compatibility of a drug or device with a particular sterilization process should be drug or device dependent if the sterilization level of the process is roughly equivalent.

The compatibility of a drug with a sterilization process is likely to vary from drug or device to drug or device and sterilization process to sterilization process. As such, selection of a sterilization process for a device incorporating a drug should be carefully considered. For example minocycline, an antibiotic commonly employed in medical devices to reduce infection associated with use or implantation of the devices, degrades to unacceptable levels under steam sterilization, but does not appear to substantially degrade with ethylene oxide sterilization. Rifampin, another antimicrobial agent that is employed in currently available implantable medical devices, is often used in combination with minocycline in medical devices to further reduce the risk of infection. Many of these rifampin-containing implantable medical devices are sterilized via treatment with ethylene oxide and numerous studies have reported no detectable degradation or no loss in antimicrobial activity when devices containing rifampin are treated with ethylene oxide.

Sterilization procedures for medical devices should be carefully selected, especially in devices that incorporate drugs. If a device incorporates more than one drug, the selection of a sterilization process can be more difficult if the drugs are incompatible with different sterilization processes. There is a need for implantable medical devices incorporating multiple drugs, which devices are produced with sterilization incompatibilities of the drugs in mind.

BRIEF SUMMARY

A system comprising an implantable medical device and a second polymeric layer configured to be disposed on or about the implantable medical device is described. The implantable medical device comprises a first polymeric layer. The first polymeric layer may form the device, such as with a catheter, or may be disposed on or about a body member of the device, such as with an infusion device or a pulse generator. The first polymeric layer may be in the form of a boot configured to be disposed around the body member of the device. A first therapeutic agent, such as minocycline, is incorporated into the first layer. A second therapeutic agent, such as rifampin, is incorporated into the second polymeric layer. The implantable medical device is sterilized by a first sterilization method such that amount of the first therapeutic agent recoverable from the device after sterilization is about 90% or more of the amount of the first therapeutic agent recoverable from the device prior to sterilization. The second polymeric layer is sterilized by a second sterilization method such that the amount of the second therapeutic agent recoverable from the second polymeric layer after sterilization is about 90% or more of the amount of the second therapeutic agent recoverable from the second polymeric layer prior to sterilization. The second polymeric layer may be in the form of a boot configured to be disposed about the implantable medical device.

A method for making a sterile implantable medical system is also described. The method comprises incorporating a first therapeutic agent in a first polymeric material and disposing the first polymeric material on or about an implantable medical device. The first polymeric material and the implantable medical device are sterilized by a first sterilization method. The method further comprises incorporating a second therapeutic material in a second polymeric material and disposing the second polymeric material on or about the sterilized first polymeric material and implantable medical device. The second polymeric material is sterilized by a second sterilization method.

A method for making a sterile catheter system is also described. The method comprises forming a catheter from a first polymeric material and incorporating a first therapeutic agent in the first polymeric material. The catheter is sterilized by a first sterilization method. The method further comprises incorporating a second therapeutic material in a second polymeric material and disposing the second polymeric material on or about the catheter. The second polymeric material is sterilized by a second sterilization method.

By using different sterilization procedures for such systems degradation of the drugs can be minimized. As degradants can pose safety concerns, especially with chronically implanted devices, it would be advantageous to minimize the production of degradants. In addition minimizing degradation of a drug or increasing the amount of drug available generally results in enhanced efficacy. These and other advantages will be readily understood from the following detailed descriptions when read in conjunction with the accompanying drawings.

BRIEF DESCRIPTION OF THE DRAWINGS

The figures are not necessarily to scale.

DETAILED DESCRIPTION

As more medical devices incorporate associated therapeutic agents, the processes for sterilizing such devices should be carefully considered, particularly for devices that contain multiple therapeutic agents. Devices, systems and methods where such consideration has been given are described herein.

Medical Device

One or more therapeutic agents may be incorporated in or on a medical device configured to release the therapeutic agent when implanted in a patient. For example, therapeutic agent may be embedded, coated, mixed, dissolved or dispersed on or in a polymeric material. The polymeric material may be disposed on, in or about at least a portion of the medical device. For example, the polymeric material may be in the form of a coating or covering. In some embodiments, the polymeric material may form the device; e.g., when the device is a catheter.

Therapeutic agent may be released from polymeric material at any rate sufficient to produce the therapeutic effect of the agent. By "release" it is meant that therapeutic agent is located at a position such that therapeutic agent may produce its therapeutic effect. In some circumstances, therapeutic agent will be considered "released" while still in contact with the polymeric material. The rate at which therapeutic agent may be released from a polymeric material into tissue may be controlled by properties of the polymeric material, as well as the manner in which therapeutic agent is disposed on or in the polymeric material. Any known or developed technology may be used to control the release rate. For example, a coating layer may be designed according to the teachings of WO/04026361, entitled "Controllable Drug Releasing Gradient Coating for Medical Devices."

Various embodiments of the invention provide an implantable medical device comprising a body member into, onto, or about which polymeric material is disposed. The medical device may be any implantable medical device, such as a lead, a stent, a catheter, a neurostimulator such as an implantable pulse generator, a pacemaker, a defibrillator, an infusion device, and the like. Therapeutic agent may be associated with the surface of the implantable medical device in any fashion such that, after implanting the device, therapeutic benefit of the agent may be experienced.

Figure 1:
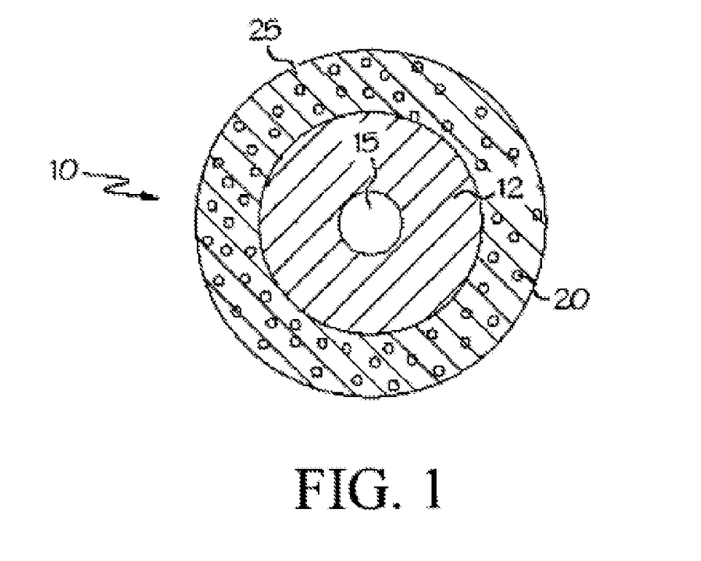
FIG. 1 is a diagrammatic illustration of a cross-section of a device comprising therapeutic agent disposed within a polymeric layer of the device.
Figure 2:
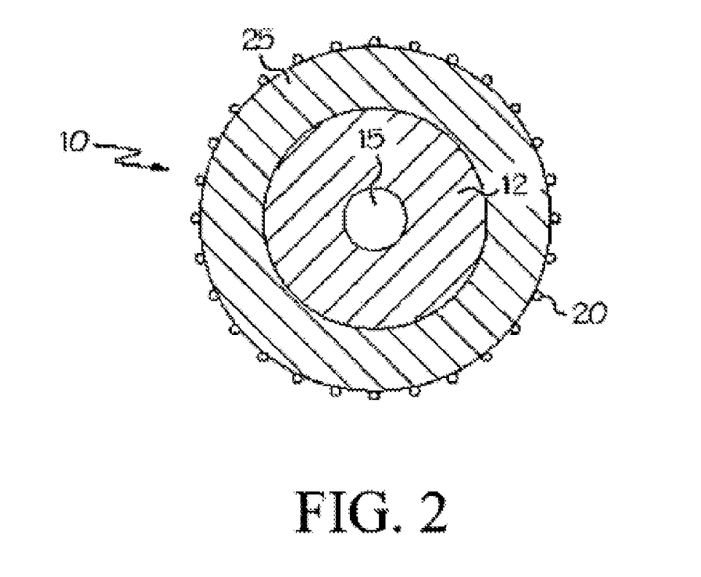
FIG. 2 is a diagrammatic illustration of a cross-section of a device comprising therapeutic agent disposed on the surface of a polymeric layer of the device.
Figure 3:
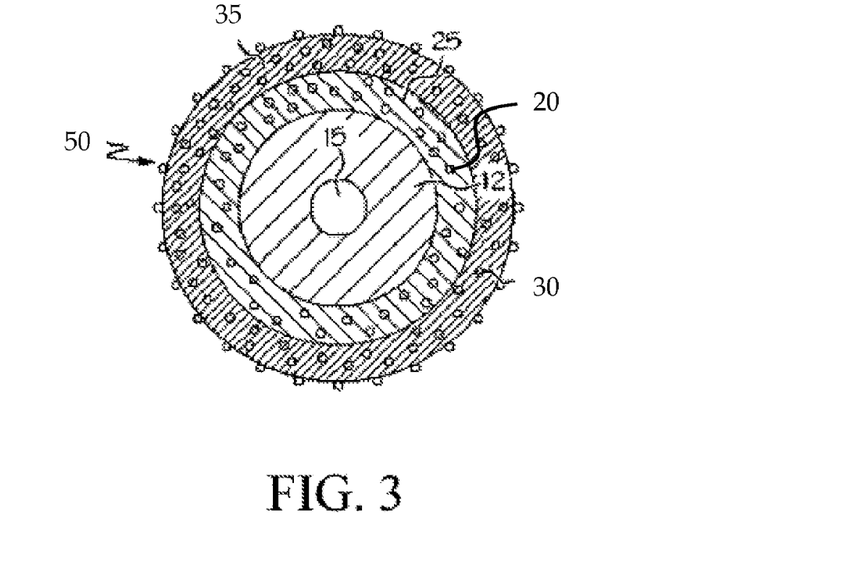
FIG. 3 is a diagrammatic illustration of a cross-section of a device comprising therapeutic agent disposed in an intermediate layer and an outer layer of the device.

For the sake of convenience, FIGS. 1-3 shown medical device 10 as a catheter comprising a lumen 15, but it should be understood that the discussion regarding these figures may be applicable to any implantable medical device 10, whether or not it comprises a lumen 15.

FIGS. 1-2 show examples of associations of a first therapeutic agent 20 with a surface of medical device 10. FIG. 1 shows that the first therapeutic agent 20 may be disposed in a first polymeric layer 25 disposed about a body member 12 of device 10. While FIG. 1 shows first therapeutic agent 20 disposed throughout the first polymeric layer 25, first therapeutic agent 20 may be disposed within one or more portions of the first polymeric layer 25 (not shown). FIG. 2 shows that first therapeutic agent 20 may be disposed on the surface of the first polymeric layer 25. While not shown, it will be understood that first therapeutic agent 20 may be disposed in body member 12 the device 10, particularly when body member 12 is made of polymeric material. For purposes of the present application, "in" or "on" will be used interchangeably to describe the position of a therapeutic agent with respect to a polymeric layer. Further, as used herein, polymeric "layer" can be in the form of a coating, boot, leave, sheath, etc. and may or may not be uniform in thickness or coverage.

FIG. 3 shows an implantable medical system 50 comprising a medical device having a body member 12 and a first polymeric layer 25. First therapeutic agent 20 is disposed in first polymeric layer 25. A second polymeric layer 35 is disposed on or about first polymeric layer 25 or device 10. Second therapeutic agent 30 is disposed in a second coating layer 35.

While not shown, it will be understood that in some embodiments, e.g. when device 10 is a catheter and body member 12 comprises polymeric material, first therapeutic agent 20 may be disposed in body member 12 and second therapeutic agent 30 may be disposed in first polymeric layer 25. That is, body member 12 serves as first polymeric layer and first polymeric layer 25 serves as second polymeric layer. It will also be understood that therapeutic agents in addition to first therapeutic agent 20 may be present in first polymeric layer 25 and therapeutic agents other than second therapeutic agent 30 may be present in second polymeric layer 35. It will be further understood that first or second therapeutic agents 20, 30 may be disposed in more than one polymeric layer of device 10 or system 50.

First or second therapeutic agents 20, 30 may be present in first or second polymeric layers 25, 35, or other layers, at any concentration. Preferably the agents are present on concentrations sufficient to produce a therapeutic effect for a desired period of time, but not at concentrations too high to cause undesired effects. Any concentration may be used. For example, first or second therapeutic agents 20, 30 may comprise about 0.1% to about 50%, or from about 1% to about 10%, of the weight of the layer. In some circumstances, it may be desirable to place a higher concentration therapeutic agent in one or more layers relative to other layers. For example, to obtain a substantially constant release rate of a therapeutic agent over time it may be desirable for an underlying layer to have a higher concentration of therapeutic agent and less in an overlying layer.

In some embodiments, first therapeutic agent 20 in first polymeric layer 25 is a faster eluting agent than second therapeutic agent 30 in second polymeric layer 35. Such a configuration will allow for first and second therapeutic agents 20, 30 to reach body tissue substantially simultaneously over prolonged periods of time. For example, with most silicone polymers, minocycline is faster eluting than rifampin. For systems 50 comprising first and second layers 20, 30 comprising silicone, it may be desirable to incorporate minocycline in the first layer 25 and rifampin in the second layer 35.

First or second polymeric layer 25, 35 or other layers may be in the form of a tube, sheath, sleeve, boot, coating, or the like. First polymeric layer 25 may be extruded, molded, coated on body member 12, grafted onto body member 12, embedded within body member 12, adsorbed to body member 12, etc. Second polymeric layer 35 may be extruded, molded, coated on first polymeric layer 25, grafted onto first polymeric layer 25, embedded within first polymeric layer 25, adsorbed to first polymeric layer 25, etc. Polymeric layers 25, 35 may be porous or non-porous. Porous materials known in the art include those disclosed in U.S. Pat. No. 5,609,629 and U.S. Pat. No. 5,591,227. Typically polymers are non-porous. However, non-porous polymers may be made porous through known or developed techniques, such as extruding with $CO_2$ or by foaming the polymeric material prior to extrusion or coating.

Examples of suitable polymeric materials that may be used to form polymeric layers 25, 35 include bioerodable or biostable polymeric materials. Suitable bioerodable polymers include as synthetic or natural bioabsorbable polymers. As used herein, "bioerodable", "biodegradable", "bioabsorbable", and the like are used interchangeably. Such polymers are recognizable and identifiable by one or ordinary skill in the art. Non-limiting examples of synthetic, biodegradable polymers include: poly(amides) such as poly(amino acids) and poly(peptides); poly(esters) such as poly(lactic acid), poly(glycolic acid), poly(lactic-co-glycolic acid), and poly(caprolactone); poly(anhydrides); poly(orthoesters); poly(carbonates); and chemical derivatives thereof (substitutions, additions of chemical groups, for example, alkyl, alkylene, hydroxylations, oxidations, and other modifications routinely made by those skilled in the art), fibrin, fibrinogen, cellulose, starch, collagen, and hyaluronic acid, copolymers and mixtures thereof The properties and release profiles of these and other suitable polymers are known or readily identifiable. It will be understood that minocycline or rifampin may elute from an intact vehicle or may be released upon degradation of the vehicle. In some embodiments, the biodegradable vehicle is a microcapsule. In another embodiment, the bioerodable vehicle is in the form of a gauze or wrap.

Suitable biostable materials include organic polymers such as silicones, polyamines, polystyrene, polyurethane, acrylates, polysilanes, polysulfone, methoxysilanes, and the like. Other polymers that may be utilized include polyolefins, polyisobutylene and ethylene-alphaolefin copolymers; acrylic polymers and copolymers, ethylene-covinylacetate, polybutylmethacrylate; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; polycarbonates; polyoxymethylenes; polyimides; polyethers; epoxy resins; polyurethanes; rayon; rayon-triacetate; cellulose; cellulose acetate, cellulose butyrate; cellulose acetate butyrate; cellophane; cellulose nitrate; cellulose propionate; cellulose ethers; carboxymethyl cellulose; polyphenyleneoxide; and polytetrafluoroethylene (PTFE). In various embodiments of the invention, the biostable vehicle comprises silicone or polyurethane.

In some embodiments, the polymeric material may be a hydrogel. Any hydrogel suitable for use in a human may be used. Hydrogels are known and recognizable by those of skill in the art. In some embodiments, the hydrogel may be a polyvinyl pyrrolidone (PVP) hydrogel.

Depending upon the type of materials used to form polymeric layers 25, 35, the layers can be applied to the surface of a body member 12 or first polymeric layer 25 through any coating processes known or developed in the art. One method includes directly bonding the coating material to a surface. By directly attaching a polymer to the body member 12 or first polymeric layer 25, covalent chemical bonding techniques may be utilized. Body member 12 or first coating layer 25 surface may possess chemical functional groups on its surface such as carbonyl groups, primary amines, hydroxyl groups, or silane groups which will form strong, chemical bonds with similar groups on polymeric material utilized. In the absence of such chemical forming functional group, known techniques may be utilized to activate the material's surface before coupling the biological compound. Surface activation is a process of generating, or producing, reactive chemical functional groups using chemical or physical techniques such as, but not limited to, ionization, heating, photochemical activation, oxidizing acids, sintering, physical vapor deposition, chemical vapor deposition, and etching with strong organic solvents. Alternatively, the first or second polymeric layer 25, 35 may be indirectly bound to body member 12 or first polymeric layer 25 through intermolecular attractions such as ionic or Van der Waals forces.

Figure 4:
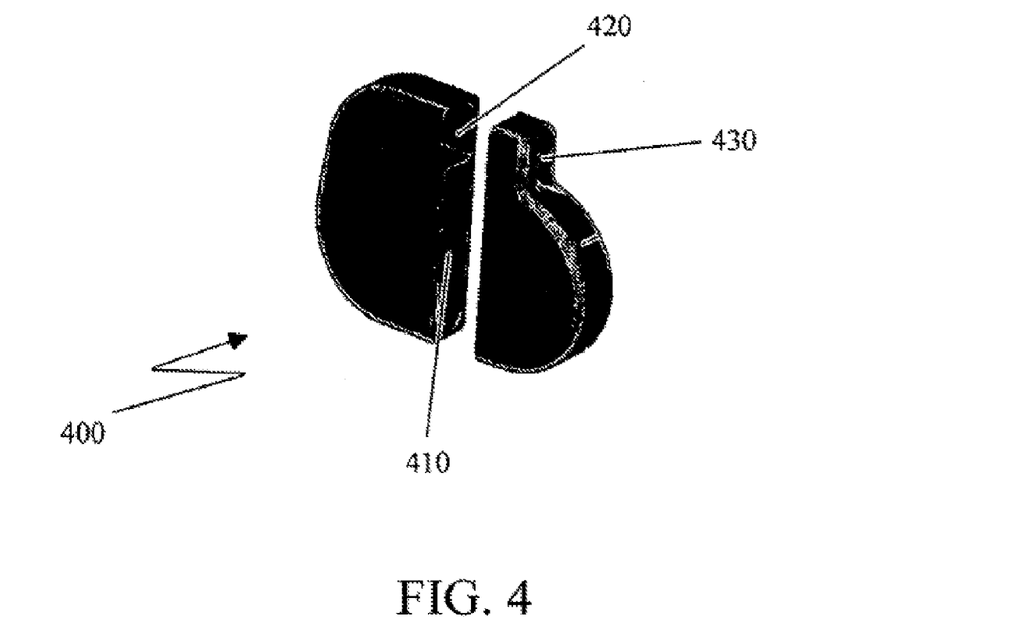
FIG. 4 is a diagrammatic illustration of a boot configured to receive an implantable medical device or portion thereof.

FIG. 4 shows an exemplary embodiment of a boot 400 configured to be disposed about an implantable medical device, such as a neurostimulator, a pacemaker, a drug infusion device, and the like. Boot 400 may be first polymeric layer 25 or second polymeric layer 35. As used herein, "or" means and/or unless otherwise indicated. Boot 400 depicted in FIG. 4 comprises an opening 410 configured to snuggly receive an implantable medical device. Boot 400 may also comprise an opening 420 for a header of the device and an opening 430 for an accessory device, such as a lead, a lead extension, or a catheter. It will be understood that boot 400 may be in any form and may be configured to be disposed about any implantable medical device.

Figure 5:
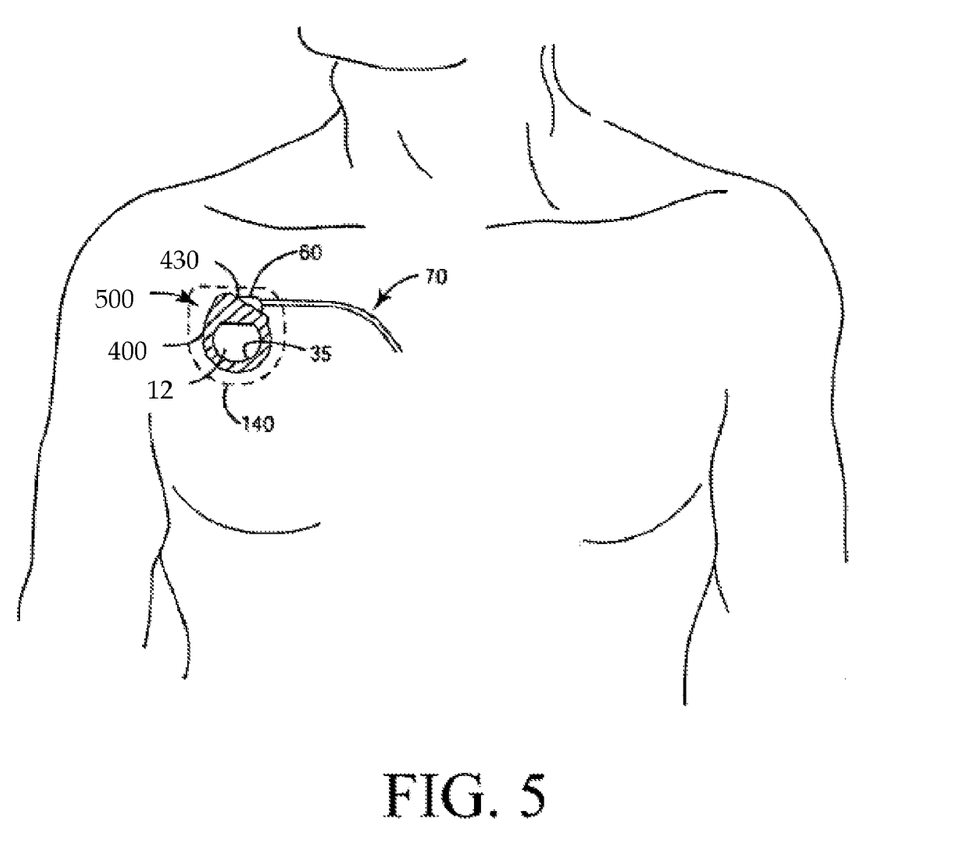
FIG. 5 is schematic view of an implantable medical device having a polymeric boot fitted over the device, the device being implanted subcutaneously in a patient.

FIG. 5 shows boot 400 fitted over the body member 12 or housing of an implantable pulse generator (IPG) 500. Boot 400 and IPG 500 are implanted into a subcutaneous pocket 140. A portion of boot 400, as depicted in FIG. 5, leaves a portion of body member 12 or housing of IPG 500 exposed through side opening 55, which allows the housing 12 to serve as a return electrode. It will be understood that in some embodiments boot 400 does not comprise a side opening 55. For example, some IPGs 500 can be operated in bipolar mode, where housing 12 does not need to serve as a return electrode. In addition boot 400 may be placed about other devices (not shown), such as an implantable infusion device, where a side opening 55 may or may not be desired. The boot 400 depicted in FIG. 5 has an edge opening 430 through which allows connection of lead 70 to connector block 60 of IPG 500. It will be understood that edge opening 430 may be similarly situated in a boot 400 for use with an infusion or other device to connect catheter or other device.

Therapeutic Agent

Therapeutic agent 20, 30 may be incorporated into a coating layer 25, 35 in a variety of ways. For example, therapeutic agent 20, 30 can be covalently grafted to a polymer of the coating layer 25, 35, either alone or with a surface graft polymer. Alternatively, therapeutic agent 20, 30 may be coated onto the surface of the polymer either alone or intermixed with an overcoating polymer. Therapeutic agent 20, 30 may be physically blended with a polymer of a polymeric layer 25, 35 as in a solid-solid solution. Therapeutic agent 20, 30 may be impregnated into a polymer by swelling the polymer in a solution of the appropriate solvent. Any means of incorporating therapeutic agent 20, 30 in a polymeric layer 25, 35 may be used, provided that therapeutic agent 20, 30 may be released, leached or diffuse from polymeric layer 25, 35 on or after contact of device 10 or system 50 with bodily fluid or tissue.

A polymer of a polymeric layer 25, 35 and therapeutic agent 20, 30 may be intimately mixed either by blending or using a solvent in which they are both soluble. This mixture can then be formed into the desired shape or coated onto an underlying structure of the medical device. One exemplary method includes adding therapeutic agent 20, 30 to a solvated polymer to form an agent/polymer solution. The agent/polymer solution can then be applied directly to the surface of body member 12 or first polymeric layer 25; for example, by either spraying or dip coating device 10. As the solvent dries or evaporates, the agent/polymer coating is deposited on body member 12. Furthermore, multiple applications can be used to ensure that the coating is generally uniform and a sufficient amount of agent has been applied to device 10.

Alternatively, a polymeric material and therapeutic agent 20, 30 are intimately mixed, either by blending or using a solvent in which they are both soluble, and coated onto body member 12 or first polymeric layer 25. Any polymeric material may be used, as long as the polymer is able to bond (either chemically or physically) to the polymer of an underlying layer of delivery element 10.

In addition, a polymer layer 25, 35 may be swelled with an appropriate solvent, allowing an agent 20, 30 to impregnate the polymer.

Therapeutic agent 20, 30 may also be covalently grafted onto a polymer of a polymeric layer 25, 35. This can be done with or without a surface graft polymer. Surface grafting can be initiated by corona discharge, UV irradiation, and ionizing radiation. Alternatively, the ceric ion method, previously disclosed in U.S. Pat. No. 5,229,172, may be used to initiate surface grafting.

Any therapeutic agent may be incorporated into a first or second polymeric layer 25, 35 according to the teachings presented herein. Examples of therapeutic agents that have been used with implantable medical devices include anti infective agents, anti-inflammatory agents and local anesthetics. A brief summary of some non-limiting classes of therapeutic agents that may be used follows.

1. Anti-Infective Agents

Any anti-infective agent may be used in accordance with the teachings described herein. As used herein, "anti-infective agent" means an agent that kills or inhibits the growth of an infective organism, such as a microbe or a population of microbes. Anti-infective agents include antibiotics and antiseptics.

A. Antibiotic

Any antibiotic suitable for use in a human may be used as described herein. As used herein, "antibiotic" means an antibacterial agent. The antibacterial agent may have bateriostatic and/or bacteriocidal activities. Nonlimiting examples of classes of antibiotics that may be used include tetracyclines (e.g. minocycline), rifamycins (e.g. rifampin), macrolides (e.g. erythromycin), penicillins (e.g. nafcillin), cephalosporins (e.g. cefazolin), other beta-lactam antibiotics (e.g. imipenem, aztreonam), aminoglycosides (e.g. gentamicin), chloramphenicol, sufonamides (e.g. sulfamethoxazole), glycopeptides (e.g. vancomycin), quinolones (e.g. ciprofloxacin), fusidic acid, trimethoprim, metronidazole, clindamycin, mupirocin, polyenes (e.g. amphotericin B), azoles (e.g. fluconazole) and beta-lactam inhibitors (e.g. sulbactam). Nonlimiting examples of specific antibiotics that may be used include minocycline, rifampin, erythromycin, nafcillin, cefazolin, imipenem, aztreonam, gentamicin, sulfamethoxazole, vancomycin, ciprofloxacin, trimethoprim, metronidazole, clindamycin, teicoplanin, mupirocin, azithromycin, clarithromycin, ofloxacin, lomefloxacin, norfloxacin, nalidixic acid, sparfloxacin, pefloxacin, amifloxacin, enoxacin, fleroxacin, temafloxacin, tosufloxacin, clinafloxacin, sulbactam, clavulanic acid, amphotericin B, fluconazole, itraconazole, ketoconazole, and nystatin. Other examples of antibiotics, such as those listed in Sakamoto et al., U.S. Pat. No. 4,642,104, which is herein incorporated by reference in its entirety, may also be used. One of ordinary skill in the art will recognize other antibiotics that may be used.

In general, it is desirable that the selected antibiotic(s) kill or inhibit the growth of one or more bacteria that are associated with infection following surgical implantation of a medical device. Such bacteria are recognized by those of ordinary skill in the art and include *Stapholcoccus aureus, Staphlococcus epidermis*, and *Escherichia coli*. Preferably, the antibiotic (s) selected are effective against strains of bacteria that are resistant to one or more antibiotic.

To enhance the likelihood that bacteria will be killed or inhibited, it may be desirable to combine two or more antibiotics. It may also be desirable to combine one or more antibiotic with one or more antiseptic. It will be recognized by one of ordinary skill in the art that antimicrobial agents having different mechanisms of action and/or different spectrums of action may be most effective in achieving such an effect. In an embodiment, a combination of rifampin and micocycline is used. In an embodiment, a combination of rifampin and clindamycin is used.

B. Antiseptic

Any antiseptic suitable for use in a human may be used in accordance with various embodiments of the invention. As used herein, "antiseptic" means an agent capable of killing or inhibiting the growth of one or more of bacteria, fungi, or viruses. Antiseptic includes disinfectants. Nonlimiting examples of antiseptics include hexachlorophene, cationic bisiguanides (i.e. chlorhexidine, cyclohexidine) iodine and iodophores (i.e. povidone-iodine), para-chloro-meta-xylenol, triclosan, furan medical preparations (i.e. nitrofurantoin, nitrofurazone), methenamine, aldehydes (glutaraldehyde, formaldehyde), silver-containing compounds (silver sulfadiazene, silver metal, silver ion, silver nitrate, silver acetate, silver protein, silver lactate, silver picrate, silver sulfate), and alcohols. One of ordinary skill in the art will recognize other antiseptics that may be employed in accordance with this disclosure.

It is desirable that the antiseptic(s) selected kill or inhibit the growth of one or more microbe that are associated with infection following surgical implantation of a medical device. Such microbes are recognized by those of ordinary skill in the art and include *Stapholcoccus aureus, Staphlococcus epidermis, Escherichia coli, Pseudomonus auruginosa*, and *Candidia*.

To enhance the likelihood that microbes will be killed or inhibited, it may be desirable to combine two or more antiseptics. It may also be desirable to combine one or more antiseptics with one or more antibiotics. It will be recognized by one of ordinary skill in the art that antimicrobial agents having different mechanisms of action and/or different spectrums of action may be most effective in achieving such an effect. In a particular embodiment, a combination of chlorohexidine and silver sulfadiazine is used.

C. Antiviral

Any antiviral agent suitable for use in a human may be used in accordance with various embodiments of the invention. Nonlimiting examples of antiviral agents include acyclovir and acyclovir prodrugs, famcyclovir, zidovudine, didanosine, stavudine, lamivudine, zalcitabine, saquinavir, indinavir, ritonavir, n-docosanol, tromantadine and idoxuridine. One of ordinary skill in the art will recognize other antiviral agent that may be employed in accordance with this disclosure.

To enhance the likelihood that viruses will be killed or inhibited, it may be desirable to combine two or more antiviral agents. It may also be desirable to combine one or more antiseptics with one or more antiviral agent.

D. Anti-Fungal

Any anti-fungal agent suitable for use in a human may be used in accordance with various embodiments of the invention. Nonlimiting examples of anti-fungal agents include amorolfine, isoconazole, clotrimazole, econazole, miconazole, nystatin, terbinafine, bifonazole, amphotericin, griseofulvin, ketoconazole, fluconazole and flucytosine, salicylic acid, fezatione, ticlatone, tolnaftate, triacetin, zinc, pyrithione and sodium pyrithione. One of ordinary skill in the art will recognize other anti-fungal agents that may be employed in accordance with this disclosure.

To enhance the likelihood that viruses will be killed or inhibited, it may be desirable to combine two or more antifungal agents. It may also be desirable to combine one or more antiseptics with one or more anti-fungal agent.

2. Anti-Inflammatory Agents

Any anti-inflammatory agent suitable for use in a human may be used in accordance with various embodiments of the invention. Non-limiting examples of anti-inflammatory agents include steroids, such as cortisone, hydrocortisone, prednisone, dexamethasone, methyl-prednisilone, an, derivatives thereof, and non-steroidal anti-inflammatory agents (NSAIDs). Non-limiting examples of NSAIDS include ibuprofen, flurbiprofen, ketoprofen, aclofenac, diclofenac, aloxiprin, aproxen, aspirin, diflunisal, fenoprofen, indomethacin, mefenamic acid, naproxen, phenylbutazone, piroxicam, salicylamide, salicylic acid, sulindac, desoxysulindac, tenoxicam, tramadol, ketoralac, flufenisal, salsalate, triethanolamine salicylate, aminopyrine, antipyrine, oxyphenbutazone, apazone, cintazone, flufenamic acid, clonixerl, clonixin, meclofenamic acid, flunixin, coichicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, and triflumidate.

3. Local Anesthetics

Any local anesthetic agent suitable for use in a human may be used in accordance with various embodiments of the invention. Non-limiting examples of local anesthetics agents include lidocaine, prilocaine, mepivicaine, benzocaine, bupivicaine, amethocaine, lignocaine, cocaine, cinchocaine, dibucaine, etidocaine, procaine, veratridine (selective c-fiber blocker) and articaine.

4. Other Pharmacological Agents

Non-limiting examples of other pharmacological agents that may be used include: beta-radiation emitting isotopes, beclomethasone, fluorometholone, tranilast, ketoprofen, curcumin, cyclosporin A, deoxyspergualin, FK506, sulindac, myriocin, 2-aminochromone (U-86983), colchicines, pentosan, antisense oligonucleotides, mycophenolic acid, etoposide, actinomycin D, camptothecin, carmustine, methotrexate, adriamycin, mitomycin, cis-platinum, mitosis inhibitors, vinca alkaloids, tissue growth factor inhibitors, platinum compounds, cytotoxic inhibitors, alkylating agents, antimetabolite agents, tacrolimus, azathioprine, recombinant or monoclonal antibodies to interleukins, T-cells, B-cells, and receptors, bisantrene, retinoic acid, tamoxifen, compounds containing silver, doxorubicin, azacytidine, homoharringtonine, selenium compounds, superoxide-dismutase, interferons, heparin; Antineoplastic/antiangiogenic agents, such as antimetabolite agents, alkylating agents, cytotoxic antibiotics, vinca alkaloids, mitosis inhibitors, platinum compounds, tissue growth factor inhibitors, cisplatin and etoposide; Immunosuppressant agents, such as cyclosporine A, mycophenolic acid, tacrolimus, rapamycin, rapamycin analogue (ABT-578) produced by Abbott Laboratories, azathioprine, recombinant or monoclonal antibodies to interleukins, T-cells, B-cells and/or their receptors; Anticoagulents, such as heparin and chondroiten sulfate; Platelet inhibitors such as ticlopidine; Vasodilators such as cyclandelate, isoxsuprine, papaverine, dipyrimadole, isosorbide dinitrate, phentolamine, nicotinyl alcohol, co-dergocrine, nicotinic acid, glycerl trinitrate, pentaerythritol tetranitrate and xanthinol; Thrombolytic agents, such as stretokinase, urokinase and tissue plasminogin activators; Analgesics and antipyretics, such as the opioid analgesics such as buprenorphine, dextromoramide, dextropropoxyphene, fentanyl, alfentanil, sufentanil, hydromorphone, methadone, morphine, oxycodone, papaveretum, pentazocine, pethidine, phenopefidine, codeine dihydrocodeine; acetylsalicylic acid (aspirin), paracetamol, and phenazone; and Antiproliferative agents such as QP-2 (taxol), paclitaxel, rapamycin, tacrolimus, everolimus, actinomycin, methotrexate, angiopeptin, vincristine, mitocycin, statins, C-MYC antisense, sirolimus, restenASE, 2-chloro-deoxyadenosine, PCNA (proliferating cell nuclear antigent) ribozyme, batimastat, prolyl hydroxylase inhibitors, halofuginone, C-proteinase inhibitors, and probucol; and combinations and/or derivates thereof.

Sterilization

First and second polymeric layers 25, 35, which contain first and second therapeutic agents 20, 30 respectively, are sterilized by different methods, where (i) first therapeutic agent 20 in first polymeric layer 25 is incompatible with the sterilization method used for second therapeutic agent 30 in second polymeric layer 35 or (ii) second therapeutic agent 30 in second polymeric layer 35 is incompatible with the sterilization method used for the first therapeutic agent 20 in first polymeric layer 25. As used herein, "incompatible", in the context of a therapeutic agent and a sterilization method, means that the therapeutic agent degrades or is not recoverable from a polymeric material after sterilization to an undesirable extent.

The underlying device 10 may be compatible with a limited number of sterilization procedures. If one of first 20 of second 30 therapeutic agents is compatible with a sterilization method with which the underlying device 10 is compatible, but the other of the first 20 or second 30 therapeutic agent is not compatible with such a sterilization method, it may be desirable to incorporate the compatible therapeutic agent into first polymeric layer 25. Device 10 with first polymeric layer 25 incorporating the compatible agent can be sterilized by one method and second polymeric layer 35 incorporating the incompatible therapeutic agent can be sterilized by another method.

In some embodiments, 80% or more of the therapeutic agent is recoverable from polymeric material after sterilization. It will be understood that if the therapeutic agent degrades, it will not be recoverable. It will be further understood that some therapeutic agent may not degrade, but nonetheless be unrecoverable. Such un-degraded, unrecoverable therapeutic agent may become so intimately associated with the polymeric material, e.g. covalently bound, that it is not able to be extracted, and thus is unrecoverable. Alternatively, with some sterilization processes; e.g. steam sterilization, therapeutic agent 20, 30 may leach out of first or second polymeric layers 25, 35, effectively reducing the amount of therapeutic agent 20, 30 that may be recovered from the polymeric layer 25, 35. In some embodiments, 85% or more of the therapeutic agent is recoverable from polymeric material after sterilization. In some embodiments, 90% or more of the therapeutic agent is recoverable from polymeric material after sterilization. In some embodiments, 95% or more of the therapeutic agent is recoverable from the polymeric material after sterilization. Of course, one therapeutic agent may be recoverable at one percentage after sterilization with one method and the other therapeutic agent may be recoverable at a different percentage after sterilization with another method. For example, 90% or more of first therapeutic agent 20 may be recoverable from the first polymeric layer 25, and 95% or more of the second therapeutic agent 30 may be recoverable from the second polymeric layer 35 (or vice versa).

Any suitable procedure for recovering minocycline or rifampin may be employed. Typically therapeutic agent 20, 30 will be extracted from polymeric material 25, 35 and the extracted product will be subject to HPLC analysis. Examples of suitable solvents for extraction include ethanol, tetrahydrofuran (THF), THF/ethanol mixtures, chloroform, toluene, ethyl acetate, and the like. Of course, preferred solvents will depend on the therapeutic agent 20, 30 and polymeric material 25, 35 used.

Any combination of therapeutic agents that are not compatible with the same sterilization method may be sterilized with different sterilization methods. The incompatibility of various therapeutic agents is known or is discoverable. For example, many implantable medical devices or systems incorporate a combination of minocycline and rifampin to reduce the infection rate following implantation. Minocycline degrades to unacceptable levels under steam sterilization, while rifampin is fairly stable under steam sterilization conditions. As such it may be appropriate to steam sterilize rifampin in, e.g. the first polymeric layer 25, and sterilize minocycline in the second polymeric layer 35 with ethylene oxide. By way of further example, it has been discovered that ethylene oxide sterilization of rifampin produces substantial degradation. See U.S. patent application Ser. No. 11/535,762, entitled "STERILIZED MINOCYCLINE AND RIFAMPIN-CONTAINING MEDICAL DEVICE", filed on even date herewith, which patent application is hereby incorporated herein by reference in its entirety. Accordingly, it may be acceptable to sterilize minocycline in, e.g., first polymeric layer 25 with ethylene oxide. However, rifampin in, e.g., second polymeric layer 35 should be sterilized by another method, e.g., irradiation, such as e-beam irradiation.

Any known or future developed sterilization method may be used in accordance with the teachings presented herein. Preferably an employed sterilization method yields a sterilized product that is safe for implantation in a human. Various guidelines have been prepared by the FDA regarding sterilization and sterility assurance requirements. Some more specific guidelines include:
1. Sterilization of healthcare products—Requirements for validation and routine control—Radiation sterilization, AAMI/ISO 11137
2. Sterilization of healthcare products—Radiation Sterilization—Selection of a sterilization dose for single production batch, AAMI/ISO TIR No. 15844
3. Medical devices—Validation and routine control of ethylene oxide sterilization, AAMI/ISO 11135
4. Biological evaluation of medical devices—Part 7: Ethylene oxide sterilization residues, AAMI/ISO 10993-7
5. Sterilization of medical devices—Microbiological methods, Part 1: Estimation of population of microorganisms on products, AAMI/ISO 11737-1
6. Sterilization of medical devices—Microbiological methods, Part 2: Tests of sterility performed in the validation of a sterilization process, AAMI/ISO 11737-2

A brief discussion of some non-limiting examples of some sterilization methods that may be used is presented below.

1. Ethylene Oxide

Any ethylene oxide (EtO) sterilization method may be used. Typically EtO sterilization is accomplished by exposing a product to 100% EtO gas. After exposure to the EtO gas, products are held in an aeration cell, where the gas disperses until the products are safe to handle. EtO sterilization processes can be tailored to handle a variety of products.

2. Gamma Radiation

Any gamma radiation sterilization method may be employed. Typically gamma radiation comprises exposing a product to gamma rays emitted from cobalt-60. Gamma radiation works well for products of varying densities, including dense products, and is very reproducible. Products sterilized with gamma radiation do not need to be verified as being sterilized due to the reliability of such sterilization procedures. For more information, see ANSI/AAMI/ISO 11137-1994.

3. E-Beam Sterilization

Any e-beam radiation sterilization method may be employed. "E-beam" or "electron-beam" radiation, as used herein, refers to a form of ionizing radiation resulting from a concentrated, high current stream of electrons generated by accelerators that produce a beam of electrons. The beam can be pulsed or continuous.

Typically, e-beam accelerators are operated at between about 3 MeV and 12 MeV. Some e-beam accelerators are capable of varying the energy at which they operate. Products are typically placed on a conveyer belt and moved through the e-beam accelerator. E-beam sterilization systems may contain sensors that allow for control of the speed of the conveyer if the e-beam current changes during processing so that the dose of e-beam radiation is held constant.

Products sterilized by e-beam radiation may not need to be subjected to sterility testing if the product is subject to the appropriate dose of e-beam radiation. Dosimeters may be used to measure the amount of radiation to which a product is exposed. For additional information, see the American National Standard, ANSI/AAMI/ISO 1137-1994.

Exemplary Methods

Figure 6:
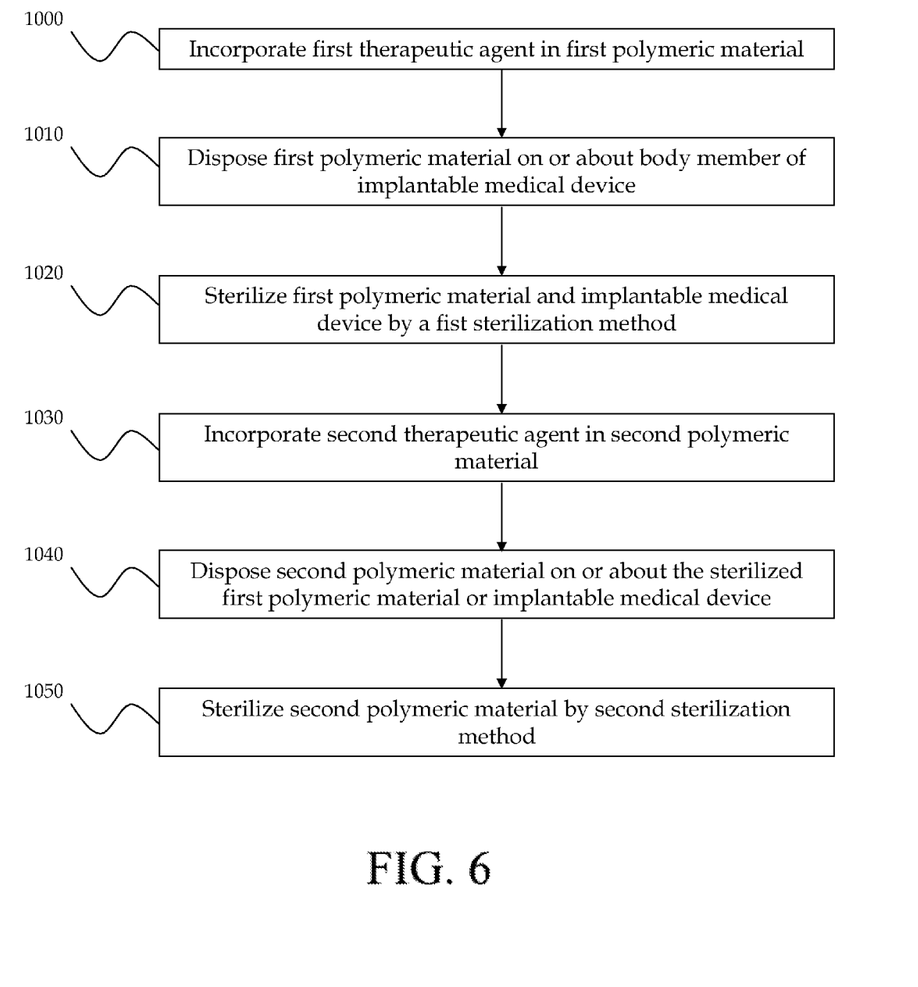
FIGS. 6-11 are flow diagrams of methods of making devices or systems having two polymeric layers, each layer having a different therapeutic agent incorporate therein.
Figure 7:
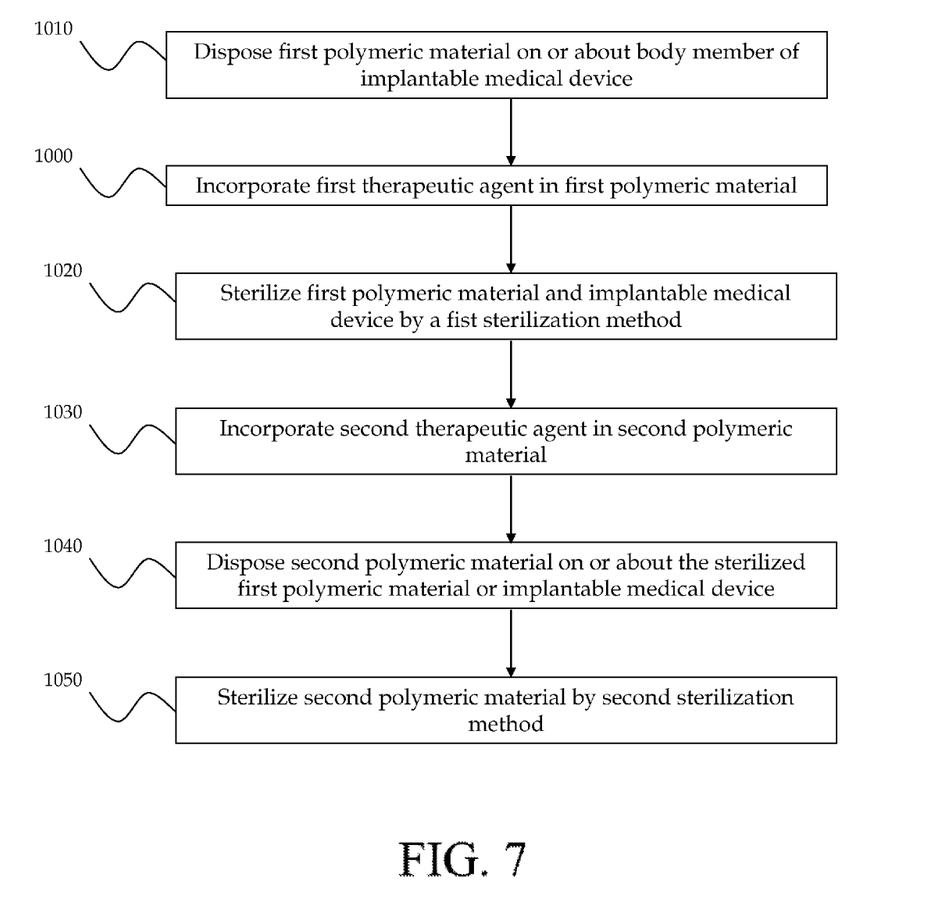
Figure 8:
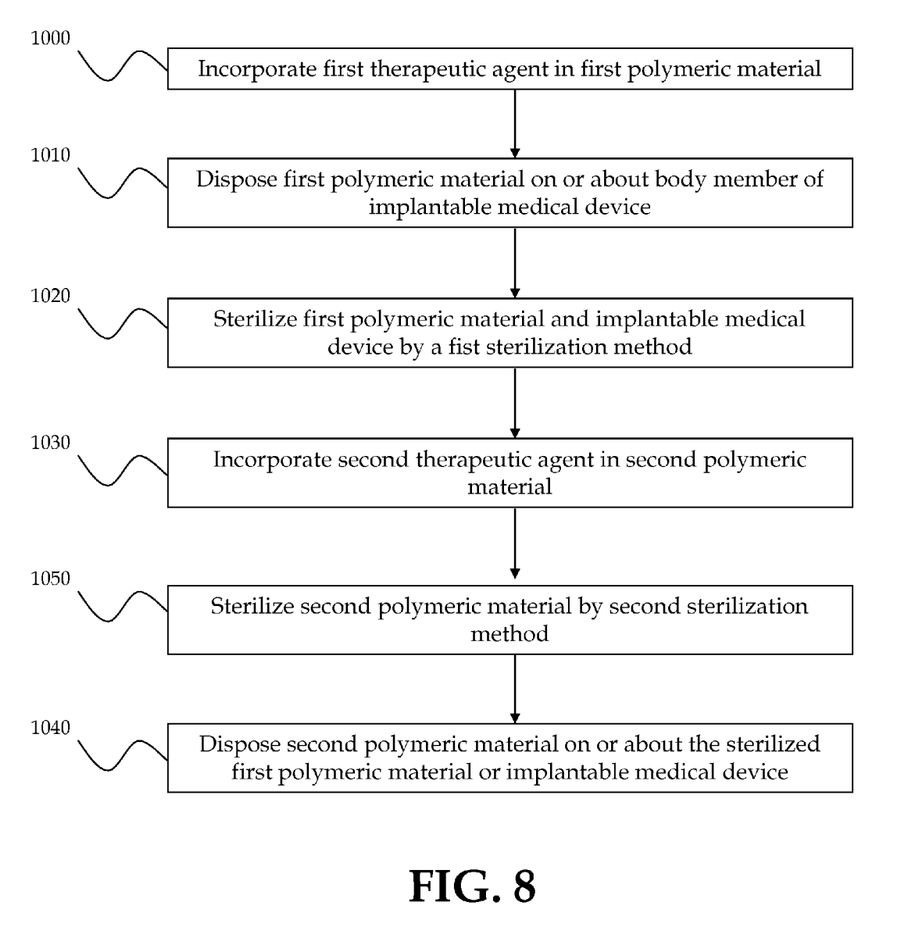

FIGS. 6-10 show exemplary methods for making implantable medical systems 50. As shown in FIG. 6, a first therapeutic agent 20 is incorporated in first polymeric material 25 (1000). The first polymeric material 25 is then disposed on or about body member 12 of implantable medical device 10 (1010). The first polymeric material 25 and medical device 10 are then sterilized by a first sterilization method (1020). Second therapeutic agent 30 is incorporated into second polymeric material 35 (1030) and the second polymeric material 35 is disposed on or about the sterilized first polymeric material 25 or implantable medical device 10 (1040). The second polymeric material 35 is then sterilized by a second sterilization method (1050). FIGS. 7 and 8 show variations on the method presented in FIG. 6. In FIG. 7, for example, the first polymeric material 25 is disposed on or about body member 12 of device 10 (1010) before the first therapeutic agent 20 is incorporated into the first polymeric material 25 (1000). In FIG. 8, the second polymeric material 35 is sterilized (1050) before being disposed on or about the sterilized first polymeric material 25 or implantable device 10 (1040). Other variations are contemplated and understood.

In some embodiments where the second polymeric layer 35 is placed on or about the first polymeric layer 25 and device 10 prior to sterilizing the second layer 35, the first polymeric material 25 may be largely impenetrable to the second sterilization method. For example, the first polymeric material 25 may be largely impermeable to ethylene oxide vapor, so that if the second polymeric material 35 (with incorporated second therapeutic agent 30) is sterilized with ethylene oxide, the ethylene oxide will have little adverse effect on the first therapeutic agent 20 incorporated in the first polymeric material 25. In situations, where the first polymeric layer 25, and thus the first therapeutic agent 20, is susceptible to the second sterilization method, it may be desirable to sterilize the second polymeric material 35 prior to disposing on or about the device 10 comprising the first polymeric material 25 with incorporated first therapeutic agent 20.

While not shown, it will be understood that the implantable medical device 10, first polymeric material 25 or the second polymeric material 35 may be packaged prior to sterilization. In some circumstances, it may be desirable to sterilize the device 10 and first polymeric layer 25 without packaging, dispose the second polymeric layer 35 about the device or first layer 25, place the device 10 with disposed layers 25, 35 in packaging and sterilize by second method designed to sterilize the second layer 35. In some circumstances, it may be desirable to sterilize the device 10 and first layer 25 in one package and sterilize the second layer 35 in a second package. The second layer 35, which may be in the form of a boot 400, can be placed about the device 10 and first layer 25 prior to implantation. By way of example, a health care professional, such as a surgeon, may place the second polymeric layer 35 about the device 10 and first layer 25 prior to implantation. Of course, other variations are contemplated and understood.

Figure 9:
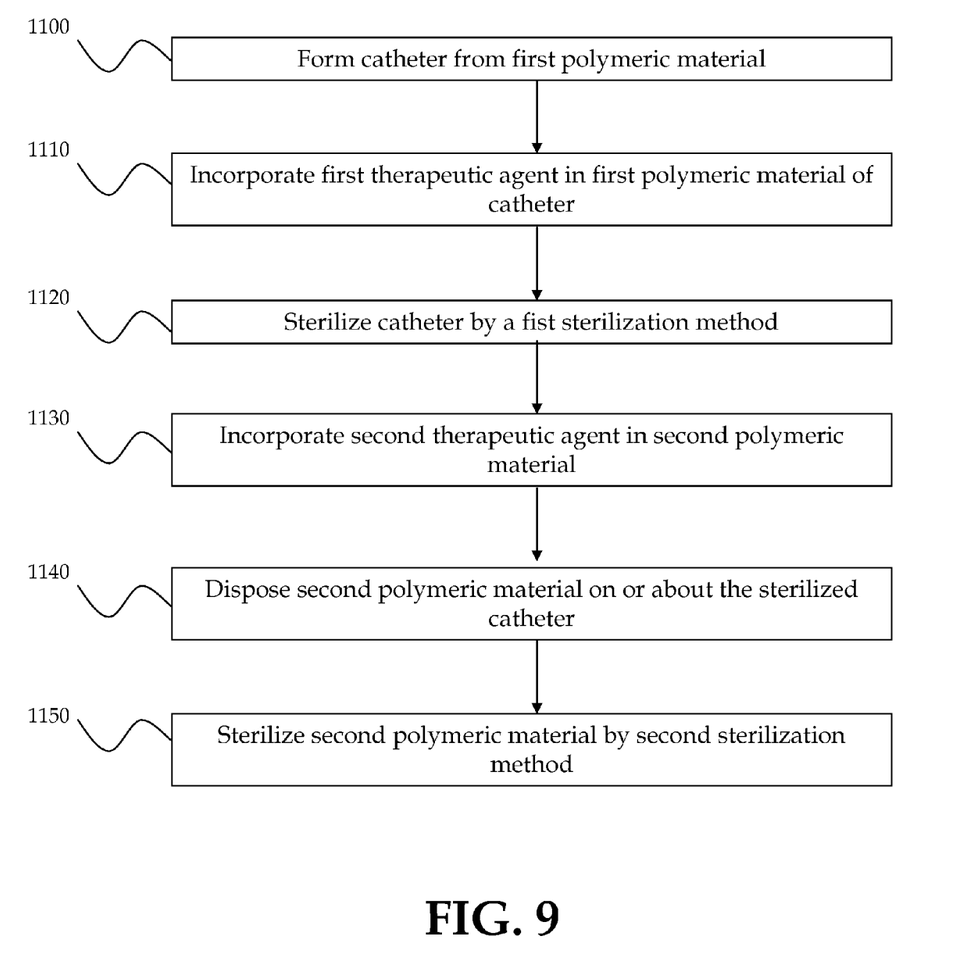
Figure 10:
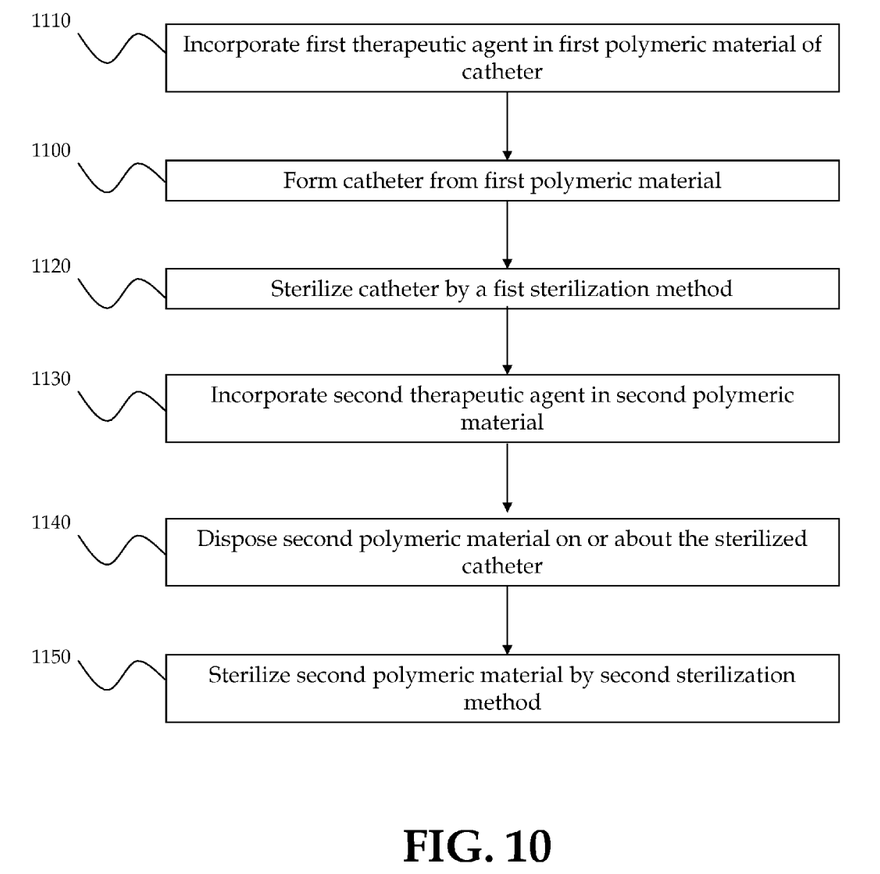
Figure 11:
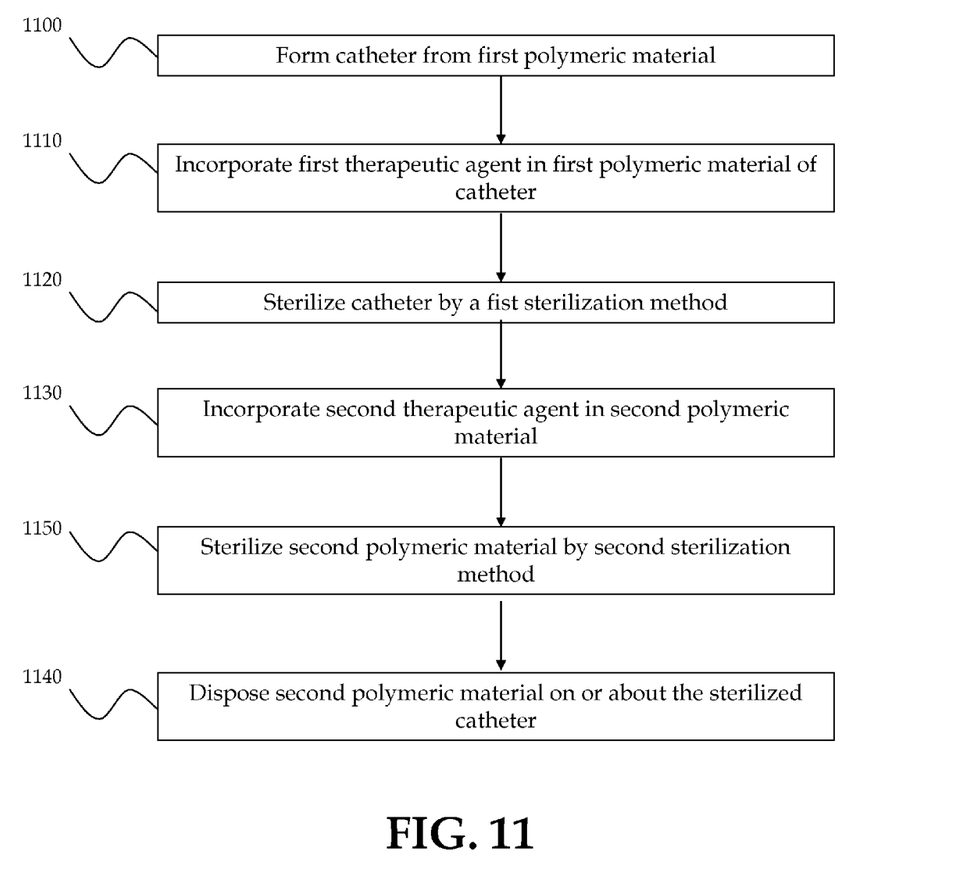

FIG. 9 shows an exemplary method for making a catheter, where first polymeric material 25 forms the implantable medical device 10, i.e. the catheter. As shown in FIG. 9, the catheter is formed from first polymeric material 25 (1100). First therapeutic agent 20 is then incorporated into first polymeric material 25 of catheter (1100). The catheter is sterilized by a first sterilization method (1120). Second therapeutic agent 30 is incorporated into second polymeric material 35 (1130). Second polymeric material 35 is disposed on or about the sterilized catheter (1140) and the second polymeric material/layer 35 is sterilized by a second sterilization method (1150). FIGS. 10 and 11 show variations on the method presented in FIG. 9. In FIG. 10, for example, the first therapeutic agent 20 is incorporated into the first polymeric material 25 (1110) before the catheter is formed (1220). In FIG. 11, the second polymeric material 35 is sterilized (1150) prior to being disposed on or about the catheter (1140). Other variations are contemplated and understood.

Thus, embodiments of the STERILIZED MINOCYCLINE AND RIFAMPIN-CONTAINING MEDICAL DEVICE are disclosed. One skilled in the art will appreciate that the methods, systems and devices described herein can be practiced with embodiments other than those disclosed. The disclosed embodiments are presented for purposes of illustration and not limitation.

What is claimed is:

1. A method comprising:
 incorporating a first therapeutic agent in a first polymeric material, wherein the first therapeutic agent is selected from minocycline and rifampin, wherein the only therapeutic agent incorporated into the first polymeric material is the minocycline or the rifampin;
 disposing the first polymeric material on or about an implantable medical device;
 sterilizing the first polymeric material and the implantable medical device by a first sterilization method,
  wherein if the first therapeutic agent is rifampin, the first sterilization method is a method other than ethylene oxide sterilization, and
  wherein if the first therapeutic agent is minocycline, the first sterilization method comprises ethylene oxide sterilization;
 incorporating a second therapeutic material in a second polymeric material,
  wherein if the first therapeutic agent is minocycline, then the second therapeutic agent is rifampin,
  wherein if the first therapeutic agent is rifampin, then the second therapeutic agent is minocycline
  wherein the only therapeutic agent incorporated into the second polymeric material is the minocycline or the rifampin;
 disposing the second polymeric material on or about the sterilized first polymeric material and implantable medical device; and
 sterilizing the second polymeric material by a second sterilization method,
  wherein if the second therapeutic agent is rifampin, the second sterilization method is a method other than ethylene oxide sterilization, and
  wherein if the second therapeutic agent is minocycline, the second sterilization method comprises ethylene oxide sterilization.

2. The method of claim 1, wherein disposing the second polymeric material on or about the sterilized first polymeric material and implantable medical device occurs after sterilizing the second polymeric material.

3. The method of claim 1, wherein disposing the second polymeric material on or about the sterilized first polymeric material and implantable medical device occurs prior to sterilizing the second polymeric material.

4. The method of claim 3, wherein disposing the second polymeric material on or about the sterilized first polymeric material and implantable medical device occurs after sterilizing the first polymeric material and implantable medical device by a first sterilization method.

5. The method of claim 1, wherein incorporating the first therapeutic agent in the first polymeric material comprises incorporating minocycline into the first polymeric material.

6. The method of claim 1, wherein sterilizing the first or second polymeric material by a method other than ethylene oxide sterilization comprises sterilizing with radiation.

7. The method of claim 6, wherein sterilizing with radiation comprises sterilizing with e-beam radiation.

8. The method of claim 1, wherein:
 incorporating the first therapeutic agent in the first polymeric material comprises incorporating minocycline into the first polymeric material;

incorporating the second therapeutic agent in the second polymeric material comprises incorporating rifampin into the second polymeric material; and disposing the second polymeric material on or about the sterilized first polymeric material and implantable medical device occurs after sterilizing the second polymeric material.

9. The method of claim 1, wherein:

incorporating the first therapeutic agent in the first polymeric material comprises incorporating minocycline into the first polymeric material; and incorporating the second therapeutic agent in the second polymeric material comprises incorporating rifampin into the second polymeric material.

10. The method of claim 1, wherein the second polymeric material is in the form of a boot and wherein disposing the second polymeric material on or about the sterilized first polymeric material and implantable medical device comprises disposing the boot about the sterilized first polymeric material and implantable medical device.

11. A method comprising:

forming a catheter from a first polymeric material;

incorporating a first therapeutic agent in the first polymeric material, wherein the only therapeutic agent incorporated into the first polymeric material is minocycline or rifampin;

sterilizing the catheter by a first sterilization method,
wherein if the first therapeutic agent is rifampin, the first sterilization method is a method other than ethylene oxide sterilization, and
wherein if the first therapeutic agent is minocycline, the first sterilization method comprises ethylene oxide sterilization;

incorporating a second therapeutic material in a second polymeric material, wherein the only therapeutic agent incorporated into the second polymeric material is minocycline or rifampin;

disposing the second polymeric material on or about the catheter; and sterilizing the second polymeric material by a second sterilization method,
wherein if the first therapeutic agent is rifampin, the first sterilization method is a method other than ethylene oxide sterilization, and
wherein if the first therapeutic agent is minocycline, the first sterilization method comprises ethylene oxide sterilization.

12. A method comprising:

incorporating minocycline in a first polymeric material, wherein minocycline is the only therapeutic agent incorporated into the first polymeric material;

disposing the first polymeric material on or about an implantable medical device selected from the group consisting of an implantable pulse generator and an implantable infusion device;

sterilizing the first polymeric material and the implantable medical device with ethylene oxide;

incorporating rifampin in a second polymeric material, wherein the second polymeric material is in the form of a boot and wherein rifampin is the only therapeutic agent incorporated into the second polymeric material;

sterilizing the second polymeric material with rifampin by a process other than ethylene oxide sterilization; and disposing the sterilized second polymeric material with rifampin on or about the sterilized first polymeric material and implantable medical device.

13. The method of claim 12, wherein sterilizing the second polymeric material with rifampin comprises sterilization with e-beam radiation.

14. The method of claim 11, wherein sterilizing the first or second polymeric material into which rifampin is incorporated comprises sterilizing the material with radiation.

* * * * *